United States Patent
Ghanem et al.

(10) Patent No.: US 8,676,289 B2
(45) Date of Patent: *Mar. 18, 2014

(54) METHOD AND APPARATUS FOR DISCRIMINATING CARDIAC SIGNALS IN A MEDICAL DEVICE BASED ON WAVELET DECOMPOSITION ANALYSIS

(75) Inventors: Raja N. Ghanem, Edina, MN (US); Troy E. Jackson, New Brighton, MN (US)

(73) Assignee: Medtronic, Inc., Minneapolis, MN (US)

(*) Notice: Subject to any disclaimer, the term of this patent is extended or adjusted under 35 U.S.C. 154(b) by 957 days.

This patent is subject to a terminal disclaimer.

(21) Appl. No.: 11/744,455

(22) Filed: May 4, 2007

(65) Prior Publication Data

US 2007/0270912 A1 Nov. 22, 2007

Related U.S. Application Data

(60) Provisional application No. 60/746,561, filed on May 5, 2006.

(51) Int. Cl.
*A61B 5/0428* (2006.01)

(52) U.S. Cl.
USPC ........... 600/373; 600/508; 600/509; 600/510; 600/515; 607/27; 607/2

(58) Field of Classification Search
USPC .............. 600/509, 508, 510, 515; 607/2, 27
See application file for complete search history.

(56) References Cited

U.S. PATENT DOCUMENTS

| | | | |
|---|---|---|---|
| 4,374,382 A | 2/1983 | Markowitz | |
| 5,117,824 A | 6/1992 | Keimel et al. | |
| 5,193,535 A | 3/1993 | Bardy et al. | |
| 5,545,186 A | 8/1996 | Olson et al. | |
| 6,067,473 A | 5/2000 | Greeninger et al. | |
| 7,774,063 B2* | 8/2010 | Ghanem et al. | 607/27 |
| 7,894,886 B2* | 2/2011 | Ghanem et al. | 600/509 |
| 2006/0111642 A1 | 5/2006 | Baura et al. | |

OTHER PUBLICATIONS

Cesar Sancez et al: "Wavelet Denoising as Preprocessing Stage to Improve ICA Performance in Atrial Fibrillation Analysis"; Independent Component Analysis and Blind Signal Separation Lecture Notes in Computer Science;;LNCS, Springer-Verlag, BE, vol. 3889, Mar. 5, 2006, pp. 486-494.*

Guler I et al: "Feature saliency using signal-to-noise raios in automated diagnostic systems developed for ECG beats"; Expert Systems With Applications, Oxford, GB, vol. 28, No. 2, Feb. 2005, pp. 295-304.*

Graps, Amara. "An Introduction to Wavelets". IEEE Computer Society. IEEE Computational Science and Engineering, Summer 1995, vol. 2, No. 2. pp. 1-18.*

"dispersion." Merriam-Webster Online Dictionary. 2010. Merriam-Webster Online. Jul. 8, 2010 <http://www.merriam-webster.com/dictionary/dispersion>.*

(Continued)

*Primary Examiner* — Allen Porter, Jr.

(74) *Attorney, Agent, or Firm* — Michael C. Soldner

(57) ABSTRACT

A method of detecting cardiac signals in a medical device that includes decomposing a cardiac signal using a wavelet function at a plurality of scales to form a corresponding wavelet transform, determining approximation coefficients in response to the plurality of scales, reconstructing a first wavelet representation of the wavelet transform using predetermined approximation coefficients of the determined approximation coefficients, and evaluating the detected cardiac signals in response to the reconstructing.

16 Claims, 7 Drawing Sheets

(56) References Cited

OTHER PUBLICATIONS

Li et al, Detection of ECG Characteristics Points Using Wavelet Transforms, IEEE Transactions on Biomedical Engineering, IEEE Service Center, Piscataway, NJ, US, vol. 42, No. 1 (Jan. 1995), pp. 21-28.

Hsieh et al, Detecting ECG Characteristic Points by Novel Hybrid Wavelet Transforms: an Evaluation of Clinical SCP-ECG Database, Computers in Cardiology 2005, IEEE Piscataway, NJ, USA (2005), p. 4.

Froese et al, Comparison of Extrasystolic ECG Signal Classifiers Using Discrete Wavelet Transforms, Pattern Recognition Letters, North Holland Publ, Amsterdam, NL, vol. 27, No. 5, (Apr. 1, 2006), pp. 393-407.

International Search Report, PCT/US20071/068255, Nov. 13, 2007, 6 Pages.

\* cited by examiner

METHOD AND APPARATUS FOR DISCRIMINATING CARDIAC SIGNALS IN A MEDICAL DEVICE BASED ON WAVELET DECOMPOSITION ANALYSIS

RELATED APPLICATION

The present application claims priority and other benefits from U.S. Provisional Patent Application Ser. No. 60/746,561, filed May 5, 2006, entitled "METHOD AND APPARATUS FOR DISCRIMINATING CARDIAC SIGNALS IN A MEDICAL DEVICE BASED ON WAVELET DECOMPOSITION ANALYSIS", incorporated herein by reference in its entirety.

CROSS-REFERENCE TO RELATED APPLICATION

Cross-reference is hereby made to the commonly-assigned related U.S. application Ser. Nos. 11/744,475, entitled "METHOD AND APPARATUS FOR DISCRIMINATING CARDIAC SIGNALS IN A MEDICAL DEVICE BASED ON WAVELET DECOMPOSITION ANALYSIS", to Ghanem et al., 11/744,484, entitled "METHOD AND APPARATUS FOR DISCRIMINATING CARDIAC SIGNALS IN A MEDICAL DEVICE BASED ON WAVELET DECOMPOSITION ANALYSIS", to Ghanem et al., both filed concurrently herewith and incorporated herein by reference in their entireties.

FIELD OF THE INVENTION

The present invention relates generally to medical devices, and more particularly to a method and apparatus for discriminating cardiac signals based on wavelet decomposition analysis.

BACKGROUND OF THE INVENTION

Lead failure (set screws, subclavian crush, header, adapter, etc.) remain a major cause of inappropriate detection and therapy in patients receiving transvenous implantable cardioverter defibrillator (ICDs). Lead failure accounts for 54% of inappropriate detection due to oversensing. Lead failure typically exhibits as saturated or signal portions with high slew rates.

ICD's detect ventricular arrhythmia whenever a specific number of short depolarization intervals is reached. For example, 12 out of 16 intervals falling into the fibrillation detection interval (FDI) will trigger VF detection at which point charging is initiated. Upon charge completion, a shock is delivered. Lead failure due to fast transients in the signal, also exhibit as short depolarization intervals which are often inappropriately detected as VF resulting in reduced specificity.

Typically, broken electrodes, lead fractures, or signal saturations demonstrate as singularities (fast transients with very large slew rates, step-like transitions) on the recorded electrograms or electrocardiograms. These are usually closely coupled and short lived. What is needed is a method and apparatus that addresses these signal characteristics (sharp fast transitions that are closely coupled in time) during wavelet decomposition analysis in order to detect lead failure.

BRIEF DESCRIPTION OF THE DRAWINGS

Aspects and features of the present invention will be appreciated as the same becomes better understood by reference to the following detailed description of the embodiments of the invention when considered in connection with the accompanying drawings, wherein.

DETAILED DESCRIPTION OF THE INVENTION

Wavelet decomposition analysis offers the unique opportunity to analyze localized time and frequency information content in the intracardiac electrogram. Using dyadic wavelet decomposition, it is possible to characterize a signal from the wavelet transform maxima. Additionally, using wavelets with increasing number of vanishing moments, it is possible to characterize the smoothness of the input signal. The local extrema in the wavelet transform correlate with the signal transients and its derivatives. The present invention relates to evaluation of the wavelet transform computed using two different mother wavelets (Haar and Daubechies $4^{th}$ order [Db4]) for the development of potential discriminators that can differentiate lead failure (or any sharp signal transients or singularities) from ventricular fibrillation (VF) by wavelet decomposition analysis.

Wavelet decomposition involves representing the given signal as a weighted superposition of linear combinations of some basis wavelets that are dilated and scaled. The weights of these bases are determined from the inner product between the given signal and the particular scaled and dilated wavelet. The basis wavelets are functions that have a zero mean, are typically of finite support (duration) and satisfy a specific condition. The wavelets are scaled and dilated to evaluate different time and frequency content information in the signal. A short duration wavelet has good time resolution but poor frequency resolution. A long duration wavelet has poor time resolution but good frequency resolution. Using wavelet decomposition, both time and frequency content can be analyzed at different scales.

Figure 1:
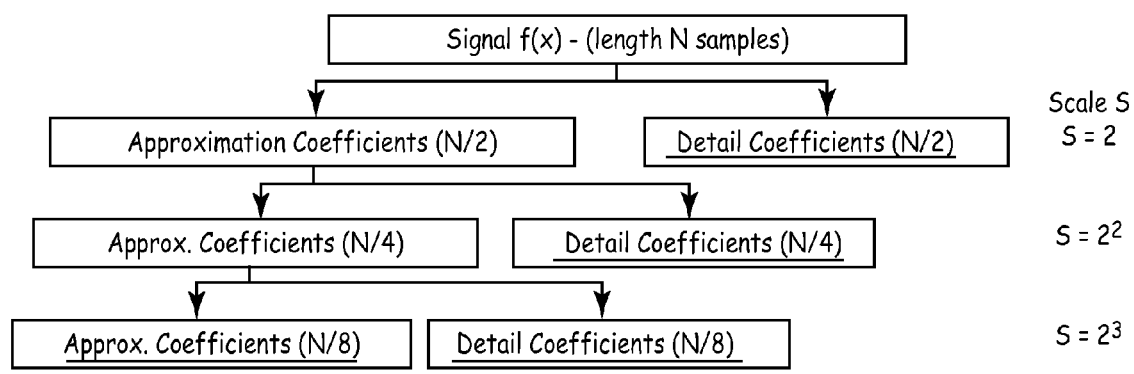
FIG. 1 is a block diagram of discrete wavelet transform decomposition utilized in a method of identifying cardiac signals according to an embodiment of the present invention.

FIG. 1 is a block diagram of discrete wavelet transform decomposition utilized in a method of identifying cardiac signals according to an embodiment of the present invention. As illustrated in FIG. 1, at each level (scale s), the signal is decomposed into a pair of approximation (lowpass frequency content) and detail (highpass frequency content) coefficients. On a subsequent level the approximation coefficients are further decomposed into approximation and detail coefficients. This process is performed up to $2^N$th level. In the example of FIG. 1, the decomposition is performed up to 3 levels implying a scale of $2^3$ as the coarse scale. The input signal f(x) is therefore completely described by: approximation coefficients (N/8), approximation coefficients (N/4), approximation coefficients (N/2), detail coefficients (N/8), detail coefficients (N/4) and detail coefficients (N/2).

By studying the detail and approximation coefficients it is possible to analyze signal characteristics during signal singularities/transients/or sharp transitions. The present invention examines the approximate coefficients at the coarse scale (approximation coefficients at N/8) and the detail coefficients at the finest scale (detail coefficients at N/2), with the detail coefficients at the finest scale providing a rate estimate and the approximation coefficients at the coarse scale providing an estimate of the variation in the average value of the signal and therefore characterizing sudden jumps.

Given that singularities are often short lived and closely coupled in time (see FIG. 2, red trace, top panel), the present invention focuses on the Haar wavelet, since it provides simplicity and ease of implementation with high temporal localization but poor frequency localization. In order to emphasize this point, a 4 times differentiable Daubechies wavelet (Db4) is included and the signal approximations are compared at the coarse scale.

The present invention assesses the effect of number of vanishing moments on the detection of wavelet transform maxima and consequently edge detection. Only 4 vanishing moments are chosen to maintain a manageable length of filter coefficients. While Db4 provides the ability to detect regularities that are differentiable 4 times, the filter size needed to implement is larger in the time domain compared to Haar. Consequently, the ability to detect short discontinuities in the signal is compromised.

The present invention accounts for the ability of Haar and Db4 wavelets to discriminate lead failure from VF using wavelet transforms (derived from the detail and approximation coefficients) at different scale levels by processing stored episode data from ICDs. The datasets consisted of runs of intracardiac near field electrograms during "simulated lead failure" and induced or spontaneous VF.

Figure 2:
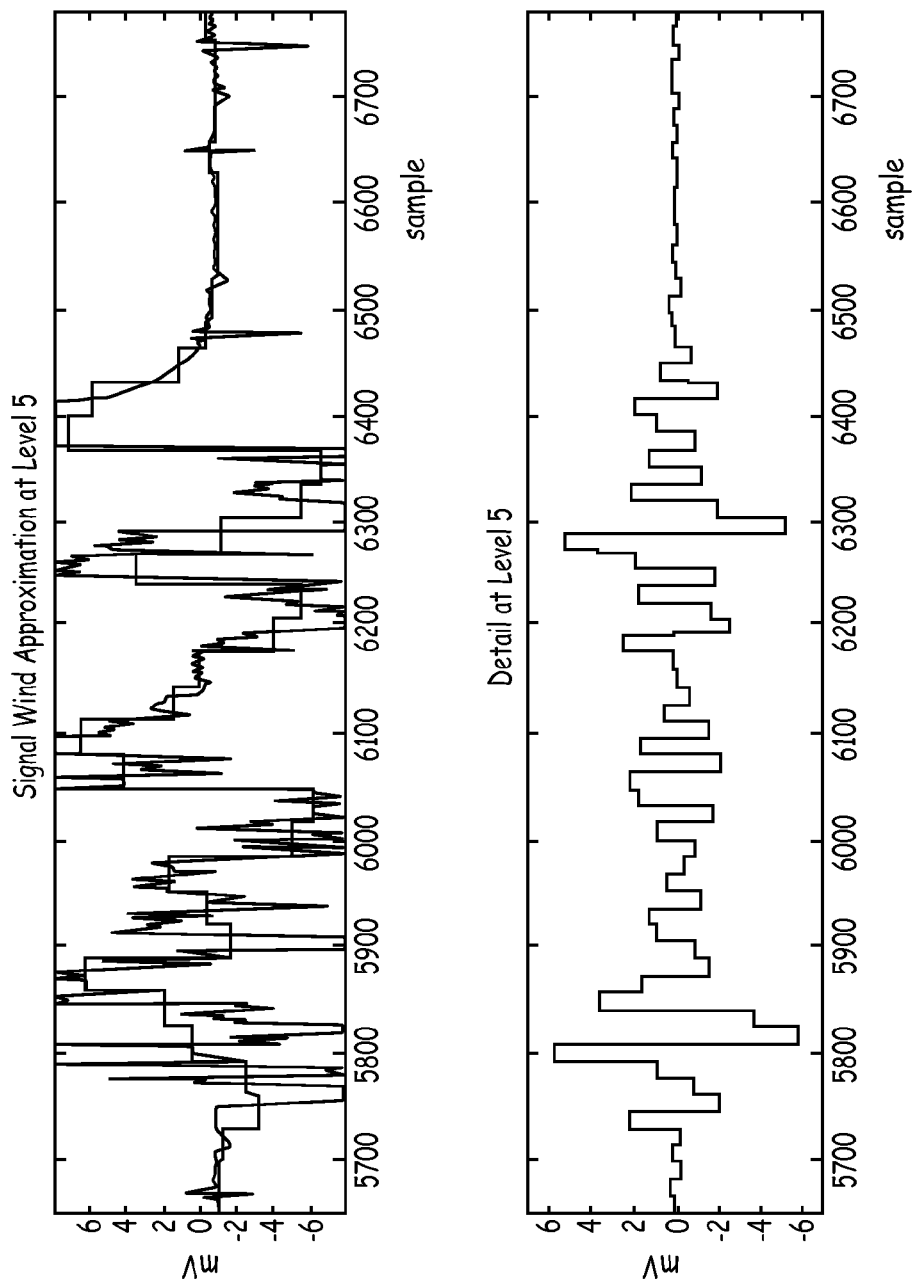
FIG. 2 is an exemplary representation of a lead failure electrogram and the corresponding wavelet decomposition.

FIG. 2 is an exemplary representation of a lead failure electrogram and the corresponding wavelet decomposition. Note that at scale level 5 (coarse scales level number 5), the wavelet transform values are large. Also, the wavelet transform maxima span all scales (level numbers in the figure) indicating high frequency content of the edges or singularities.

The wavelet reconstruction from the lowpass coefficients at detail level 5 is overlaid in blue. Wavelet transform coefficients at detail 5 are shown in the middle panel. Wavelet transform scale-time representation is shown at 5 different scales in the bottom panel.

Figure 3:
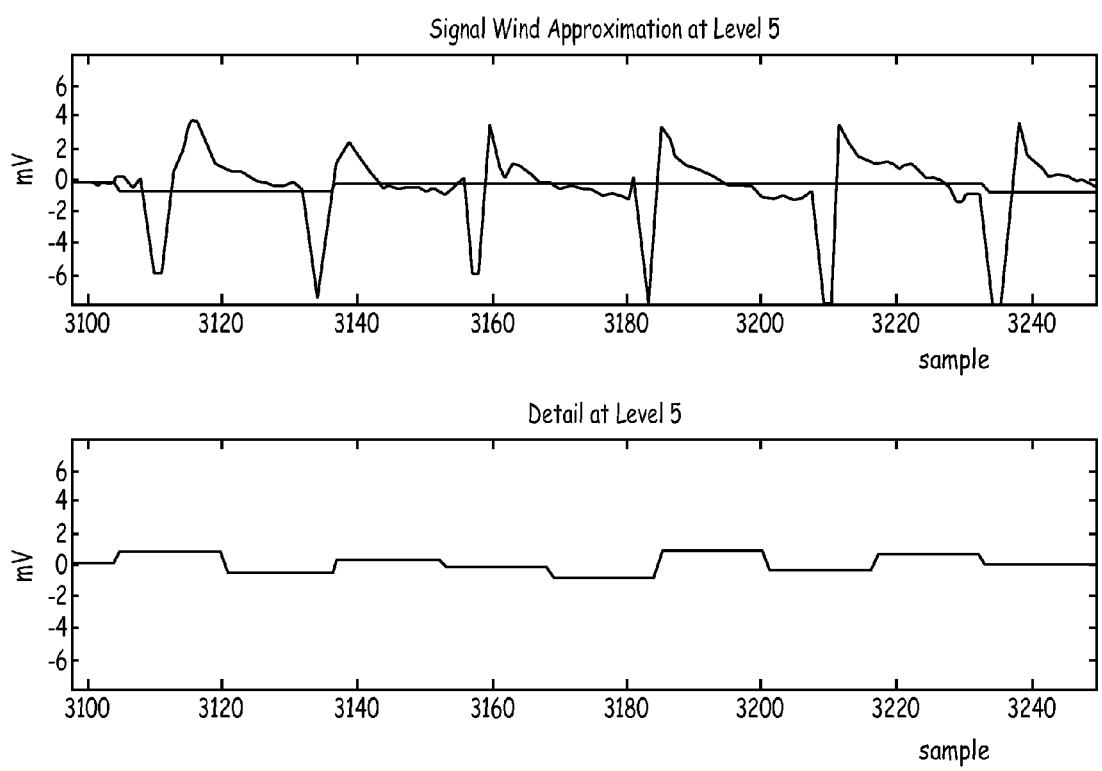
FIG. 3 is an exemplary representation of a ventricular fibrillation electrogram and the corresponding wavelet decomposition.

FIG. 3 is an exemplary representation of a ventricular fibrillation electrogram and the corresponding wavelet decomposition. As illustrated in FIG. 3, wavelet transform coefficients at smaller scales (finest scale) track the R-waves and can therefore be used to determine the ventricular rate. This is expected because at finer scales the wavelet support is narrow enough to capture the fast slew rates in the R-waves.

By applying the Haar wavelet and computing the detail (highpass) and approximation (lowpass) representations, statistical measures are then derived on the wavelet transform in order to discriminate signal singularities from VF. At fine scales, the wavelet transform details represent the ventricular depolarizations (R-waves). At coarse scales, the wavelet transform approximations represent the DC shift or average value of the signal.

Figure 4:
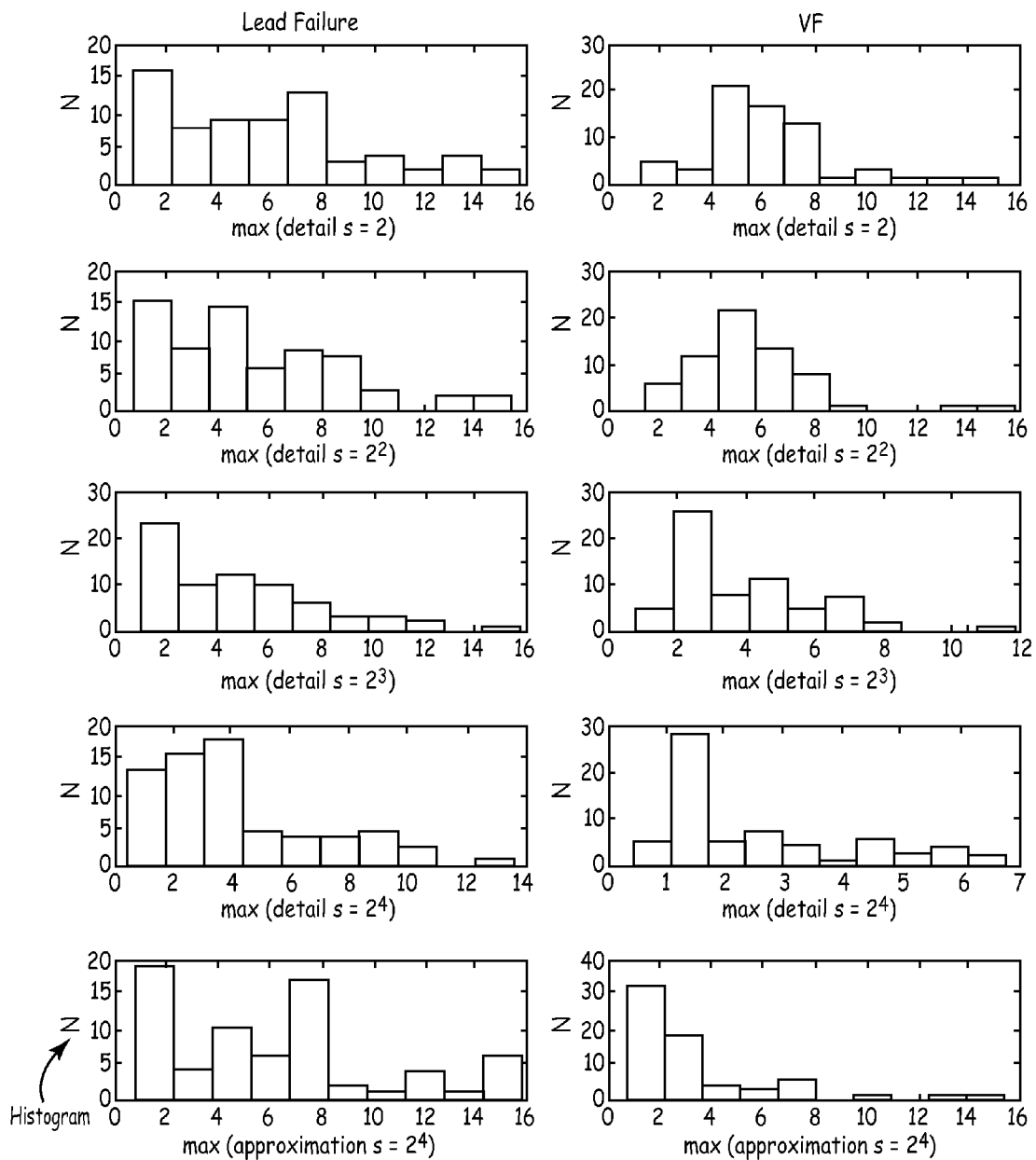
FIG. 4 is a histogram of the maximum of the absolute value of the wavelet details representation (d1 through d4) at various scales as well as the approximation coefficients representation (a4) for lead failure and ventricular fibrillation data.

FIG. 4 is a histogram of the maximum of the absolute value of the wavelet details representation (d1 through d4) at various scales as well as the approximation coefficients representation (a4) for lead failure and ventricular fibrillation data. Note that at the scale level 4 (a4), a large percentage of approximation coefficients are less than 4 during VF while a smaller percentage of the corresponding coefficients is less than 4 during lead failure. Note that in certain lead failure cases the signal may still intermittently conduct, then this percentage must be interpreted as an overestimate.

Because lead failure can contain segments with minimal transients, then low coefficients can be present and this may explain why some percentage of the approximation are also less than 4, while a majority of approximation coefficients are below 4 for ventricular fibrillation (VF).

Figure 5:
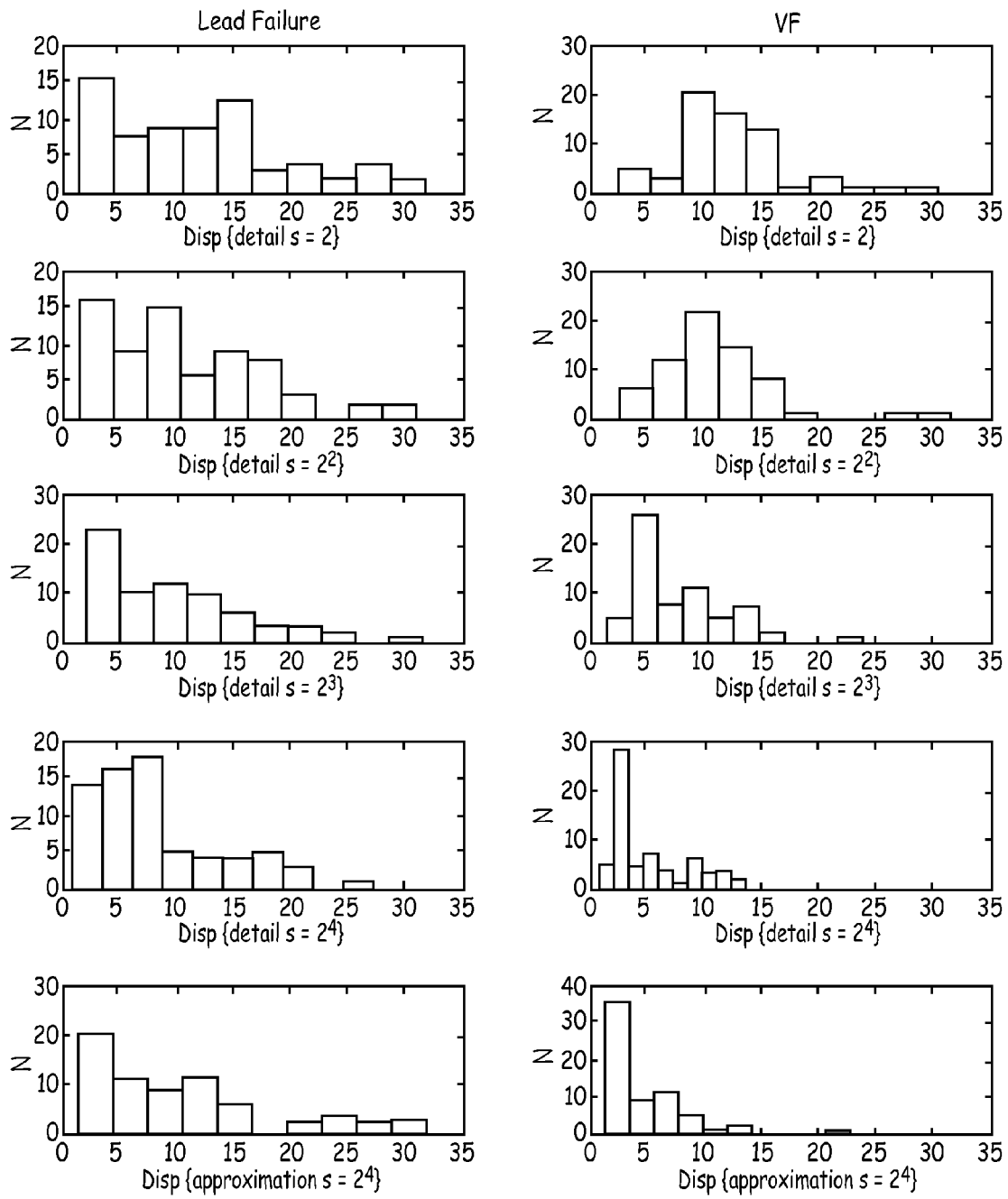
FIG. 5 shows the histograms of the dispersion of the wavelet details and approximation reconstructions during lead failure (LF) and ventricular fibrillation (VF) at various scales using the Haar wavelets.

FIG. 5 shows the histograms of the dispersion of the wavelet details and approximation reconstructions during lead failure (LF) and ventricular fibrillation (VF) at various scales using the Haar wavelets. Dispersion was computed as the maximum wavelet transform coefficient minus the minimum wavelet transform coefficient. FIG. 5 displays this dispersion at various scale levels.

Figure 6:
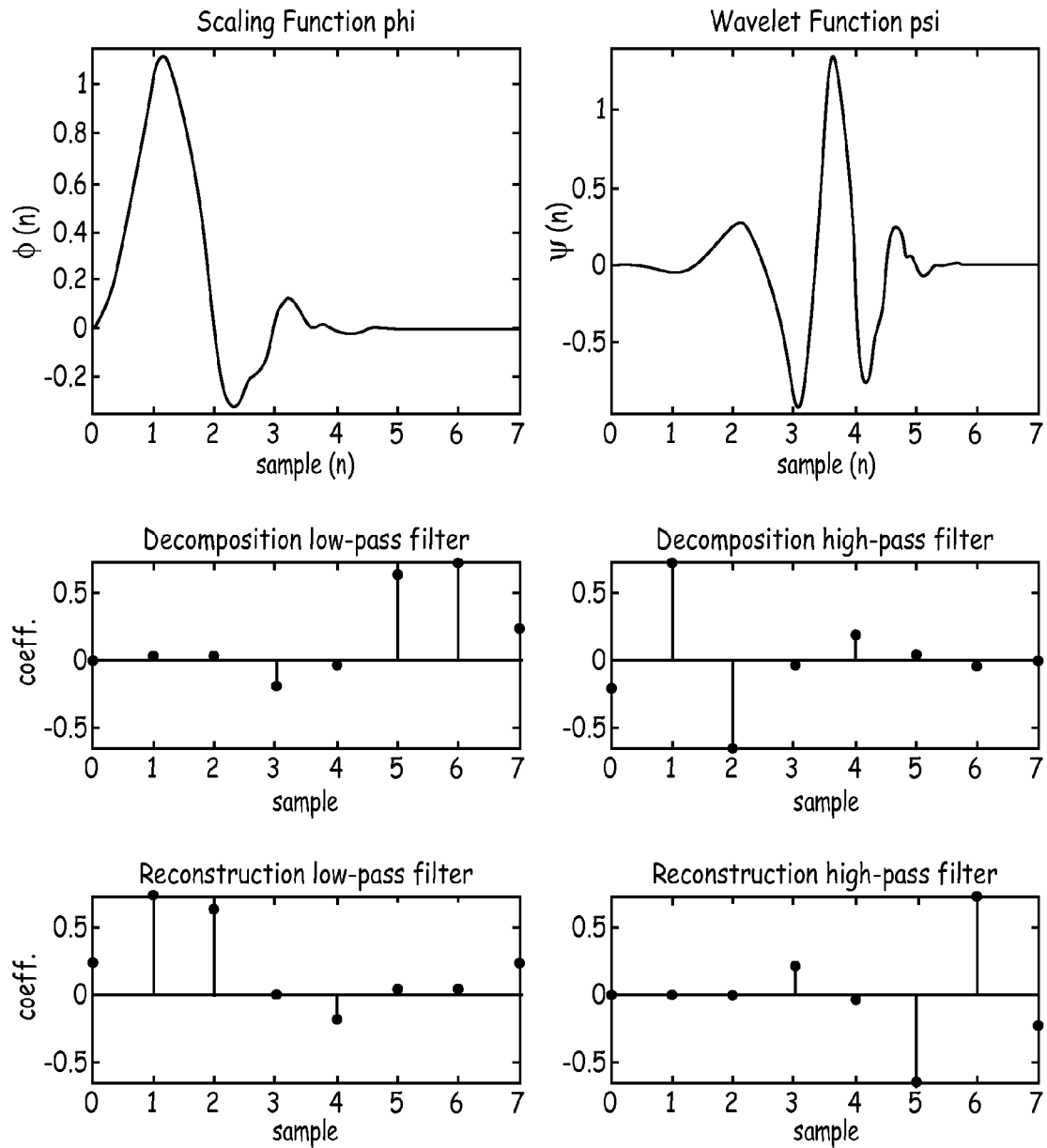
FIG. 6 is a schematic diagram of a Daubechies (Db4, $4^{th}$ order) wavelet.

The Haar wavelet is known to have 1 vanishing moment and as such is suitable for representing irregular transients in the time domain. However, it's not suitable to represent the smoothness in the signal. That is, while the Haar wavelet may be ideal for detecting step like transients in the signal, it is not as suitable to characterize slowly varying VF. In order to study the effect of the number of vanishing moments on the wavelet decomposition, we consider the Daubechies (Db4, $4^{th}$ order) wavelet. FIG. 6 shows Db4.

Figure 7:
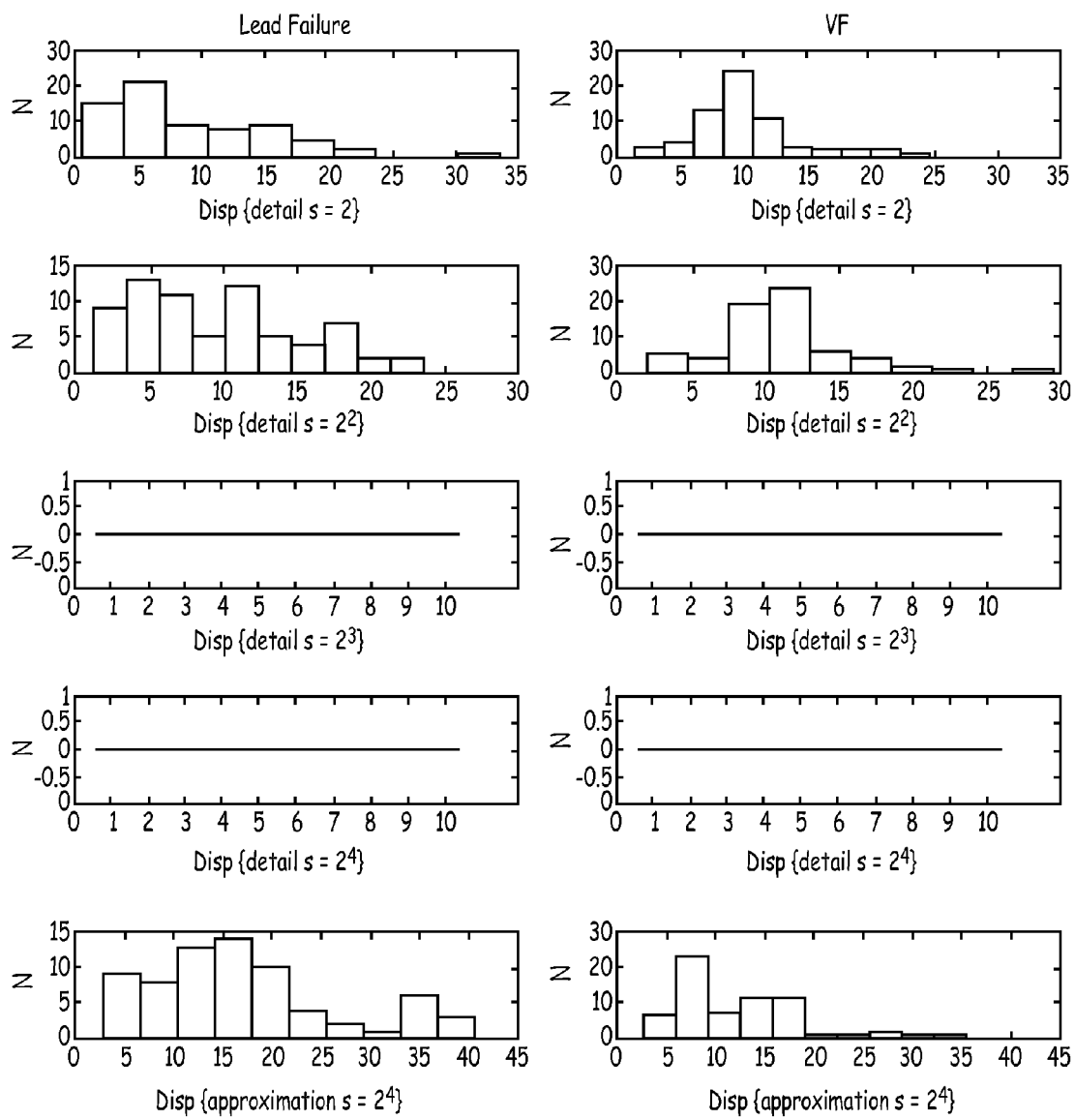
FIG. 7 shows the histograms of the dispersion of the detail and approximation wavelet representations during lead failure (LF) and ventricular fibrillation (VF) using the Daubechies (Db4, $4^{th}$ order) wavelet.

FIG. 7 shows the histograms of the dispersion of the detail and approximation wavelet representations during lead failure (LF) and ventricular fibrillation (VF) using the Db4 wavelet. Because the wavelet is 4 times differentiable it characterizes the smoothness of the input signal better than the Haar wavelet. This is evident from the wide spread of the dispersion of coefficients during VF at the finest scale approximation coefficients (level a2). This spread is larger compared to that seen using the Haar. This implies that a higher order wavelet characterize better the smoothness of the signal than an irregular one. For the purpose of singularity detection, however, the Haar wavelet may be a better choice.

Early lead failure algorithms have incorporated lead impedance measurements (as a surrogate to lead quality: high values signify open circuit or broken lead) and number of short RR interval counts (RR is defined as the time interval between consecutive depolarization, i.e. R-waves). However, it is not possible to measure electrode impedance when pacing circuitry is not available. More recent algorithms rely on measurements made on the far field electrogram when the sensed rate from the near field electrogram falls in the VF shock zone. In the present invention, a potential approach for lead failure detection utilizes the near field electrogram without relying on far field electrogram measurements. The potential for this approach lies in the possibility to detect electrode failure when impedance measurements through the electrode to assess tissue/electrode/lead functionality are not possible. In addition, this approach could be used to detect sudden transients in the ECG or electrogram and therefore preclude the need for blanking post pace or post shock. Today's ICDs blank the sensing amplifier hardware post pacing or post shock in order not to sense the recovery from polarization which often exhibits as sharp and fast transients. Using the technique presented by the present invention, polarization, like singularities, can be detected and detection can be withheld accordingly without the need to blank the sensing amplifiers.

In order to detect short durations of signal discontinuities, it is essential to choose a wavelet function such that the length of the lowpass and highpass wavelet decomposition filters is short. This is shown in the histogram of the dispersion of the wavelet transform at the approximation level a2 when using the Db4 wavelet versus the Haar wavelet at level a4. At that scale level, larger dispersions are found with Db4 (FIG. 7, right column, a2) as compared to Haar (FIG. 4, right column, a4). This is expected because in some instances VF exhibits as a smoothly varying frequency signal. The use of the wavelet transform represents a signal that is a mix of sharp transients and slowly varying components as is the case with lead failure, saturated signals, or signals recovering post shock due to electrode polarization.

According to the present invention, it is feasible to use wavelet decomposition to characterize lead failure (or more generally singularities in the signal) and to potentially discriminate that from ventricular fibrillation. Here, we recommend using the Haar wavelet because it is an irregular wavelet that would be suitable for detecting singularities.

In a method of identifying cardiac signals according to an embodiment of the present invention, a cardiac signal is decomposed using a first wavelet function at a first plurality of scales to form a corresponding wavelet transform. First approximation and detail coefficients are determined in response to the first plurality of scales.

In another embodiment of the present invention, a cardiac signal is decomposed using a first wavelet function at a first plurality of scales to form a corresponding wavelet transform, and first approximation coefficients are determined in response to the first plurality of scales. A comparison of dispersion associated with the determined first approximation coefficients is then made.

According to an embodiment of the present invention, a wavelet representation of the wavelet transform is reconstructed using predetermined approximation coefficients of the determined first approximation coefficients, wherein the comparing is in response to the reconstructed wavelet representation. In another embodiment, the cardiac signal is decomposed using a first wavelet function at a first plurality of scales to form a corresponding wavelet transform, first approximation coefficients are determined in response to the first plurality of scales and the dispersion associated with the determined first approximation coefficients are determined. Then the cardiac signal is decomposed using a second wavelet function at a second plurality of scales to form a corresponding second wavelet transform, second approximation coefficients are determined in response to the second plurality of scales, and dispersion associated with the determined second approximation coefficients is compared.

According to an embodiment of the present invention, a wavelet representation of the second wavelet transform is constructed using predetermined approximation coefficients of the determined second approximation coefficients, wherein the comparing dispersion associated with the determined second approximation coefficients is in response to the reconstructed wavelet representation of the second wavelet transform. The compared dispersion associated with the reconstructed wavelet representation of the first wavelet transform and the reconstructed wavelet representation of the second wavelet transform is then analyzed.

According to the present invention the cardiac signal is identified as being associated with ventricular fibrillation in response to the compared dispersion being less than a dispersion threshold, and the cardiac signal is identified as being associated with a corruption of a lead in response to the compared dispersion not being less than the dispersion threshold.

It is understood that, according to the present invention, the first approximation coefficients may be either the same or different than the second approximation coefficients.

While a particular embodiment of the present invention has been shown and described, modifications may be made. It is therefore intended in the appended claims to cover all such changes and modifications, which fall within the true spirit and scope of the invention.

We claim:

1. A method of detecting faults in a lead of an implantable medical device, an electrode being positioned with respect to the lead, comprising the steps of:
    sensing electrical signals with the electrode;
    obtaining a signal function based on the electrical signal;
    applying a wavelet transform function to the signal function to obtain a plurality of highpass wavelet values and a plurality of lowpass wavelet values associated with the signal function; then applying a wavelet transform function to an immediately preceding plurality of lowpass wavelet values associated with the signal function to obtain a subsequent plurality of highpass wavelet values and a subsequent plurality of lowpass wavelet values associated with the signal function; then
    repeating at least once the applying the wavelet transform function to an immediately preceding plurality of lowpass wavelet values associated with the signal function;
    calculating a dispersion of the lowpass wavelet values; and
    identifying a fault in the lead of the implantable medical device based, at least in part, on the dispersion of the lowpass wavelet values.

2. The method of claim 1, further comprising the step of:
    creating a wavelet representation of the signal function by combining at least one of the pluralities of lowpass wavelet values;
    wherein the calculating a dispersion step comprises calculating a dispersion of wavelet values of the wavelet representation.

3. The method of claim 1, further comprising:
    applying a second wavelet transform function to the signal function to obtain a second plurality of highpass wavelet values and a second plurality of lowpass wavelet values associated with the signal function; then
    applying a second wavelet transform function to an immediately preceding second plurality of lowpass wavelet values associated with the signal function to obtain a subsequent second plurality of highpass wavelet values and a subsequent second plurality of lowpass wavelet values associated with the signal function; then
    repeating at least once the applying the second wavelet transform function to an immediately preceding second plurality of lowpass wavelet values associated with the signal function; and
    calculating a second dispersion of the second lowpass wavelet values;
    wherein the identifying step identifies a fault in the lead of the implantable medical device based, at least in part, on the dispersion of the lowpass wavelet values and the second dispersion of the second lowpass wavelet values.

4. The method of claim 3, further comprising the step of:
    creating a wavelet representation of the signal function by combining at least one of the second pluralities of lowpass wavelet values;

wherein the calculating a dispersion step comprises calculating a dispersion of wavelet values of the wavelet representation.

5. The method of claim 3, wherein the wavelet transform function is different than the second wavelet transform function.

6. The method of claim 1, further comprising the step of:
comparing the dispersion of the lowpass wavelet values with a dispersion threshold to obtain a comparison; and
wherein the identifying step comprises identifying ventricular fibrillation if the comparison is less than a dispersion threshold identifying a fault in the lead of the implantable medical device if the comparison is not less than the dispersion threshold.

7. The method of claim 1, wherein the wavelet transform function is a Haar wavelet transform function.

8. A method of detecting faults in a lead of an implantable medical device, an electrode being positioned with respect to the lead, comprising the steps of:
sensing electrical signals with the electrode;
obtaining a signal function based on the electrical signal;
applying a wavelet transform function to the signal function to obtain a plurality of highpass wavelet values and a plurality of lowpass wavelet values associated with the signal function; then applying a wavelet transform function to an immediately preceding plurality of lowpass wavelet values associated with the signal function to obtain a subsequent plurality of highpass wavelet values and a subsequent plurality of lowpass wavelet values associated with the signal function; then
repeating at least once the applying the wavelet transform function to an immediately preceding plurality of lowpass wavelet values associated with the signal function;
creating a first wavelet representation of the signal function by combining at least one of the pluralities of lowpass wavelet values; and identifying a fault in the lead of the implantable medical device based, at least in part, on the first wavelet representation.

9. The method of claim 8, further comprising:
creating a second wavelet representation of the signal function by combining at least one of the pluralities of highpass wavelet values; and
wherein the identifying a fault in the lead step is based, at least in part, on the first wavelet representation and the second wavelet representation.

10. The method of claim 9, wherein the at least one of the pluralities of lowpass wavelet values of the creating a first wavelet representation step are the plurality of lowpass wavelet values obtained in the applying a wavelet transform function to the signal function step; and
wherein the at least one of the pluralities of highpass wavelet values of the creating a second wavelet representation step are the plurality of highpass wavelet values obtained in a final repeating of the applying a wavelet transform function to an immediately preceding plurality of lowpass wavelet values step.

11. The method of 8, wherein the wavelet transform function is a Haar wavelet transform function.

12. The method of claim 11, wherein the least one of the pluralities of lowpass wavelet values of the creating a first wavelet representation step are the plurality of lowpass wavelet values obtained in the applying a wavelet transform function to the signal function step; and
wherein at least one of the pluralities of highpass wavelet values of the creating a second wavelet representation step are the plurality of highpass wavelet values obtained in a second repeating of the applying a wavelet transform function to an immediately preceding plurality of lowpass wavelet values step.

13. A method of detecting faults in a lead of an implantable medical device, an electrode being positioned with respect to the lead, comprising:
sensing electrical signals with the electrode;
obtaining a signal function based on the electrical signal;
applying a wavelet transform function to the signal function to obtain a plurality of highpass wavelet values and a plurality of lowpass wavelet values associated with the signal function; then applying a wavelet transform function to an immediately preceding plurality of lowpass wavelet values associated with the signal function to obtain a subsequent plurality of highpass wavelet values and a subsequent plurality of lowpass wavelet values associated with the signal function; then
repeating at least once the applying the wavelet transform function to an immediately preceding plurality of lowpass wavelet values associated with the signal function;
creating a first wavelet representation of the signal function by combining at least one of the pluralities of lowpass wavelet values; and creating a second wavelet representation of the signal function by combining at least one of the pluralities of highpass wavelet values; and
calculating a first dispersion of the first wavelet representation and a second dispersion of the second wavelet representation; and
identifying a fault in the lead of the implantable medical device based, at least in part, on the first dispersion and the second dispersion.

14. The method of claim 13, wherein at least one of the pluralities of lowpass wavelet values of the creating a first wavelet representation step are the plurality of lowpass wavelet values obtained in the applying a wavelet transform function to the signal function step; and
wherein the at least one of the pluralities of highpass wavelet values of the creating a second wavelet representation step are the plurality of highpass wavelet values obtained in a final repeating of the applying a wavelet transform function to an immediately preceding plurality of lowpass wavelet values step.

15. The method of 13, wherein the wavelet transform function is a Haar wavelet transform function.

16. The method of claim 15, wherein the least one of the pluralities of lowpass wavelet values of the creating a first wavelet representation step are the plurality of lowpass wavelet values obtained in the applying a wavelet transform function to the signal function step; and
wherein at least one of the pluralities of highpass wavelet values of the creating a second wavelet representation step are the plurality of highpass wavelet values obtained in a second repeating of the applying a wavelet transform function to an immediately preceding plurality of lowpass wavelet values step.

* * * * *

UNITED STATES PATENT AND TRADEMARK OFFICE
CERTIFICATE OF CORRECTION

| | | |
|---|---|---|
| PATENT NO. | : 8,676,289 B2 | Page 1 of 1 |
| APPLICATION NO. | : 11/744455 | |
| DATED | : March 18, 2014 | |
| INVENTOR(S) | : Raja N. Ghanem et al. | |

It is certified that error appears in the above-identified patent and that said Letters Patent is hereby corrected as shown below:

In the Claims

Col. 7, line 57, delete "The method of 8, wherein" and insert in place thereof -- The method of claim 8, wherein --;

Col. 8, line 48, delete "The method of 13, wherein" and insert in place thereof -- The method of claim 13, wherein --;

Col. 8, line 50, delete "The method of claim 15, wherein the least one" and insert in place thereof -- The method of claim 15, wherein at least one --.

Signed and Sealed this
Twenty-ninth Day of March, 2016

Michelle K. Lee
*Director of the United States Patent and Trademark Office*